United States Patent
Lenihan et al.

(10) Patent No.: US 8,470,025 B2
(45) Date of Patent: Jun. 25, 2013

(54) CARDIOVASCULAR PROCEDURES

(75) Inventors: Tim Lenihan, Hradec Kralove (CZ);
Mathias Wilhelmi, Isernhagen (DE);
Axel Haverich, Hannover (DE)

(73) Assignee: Contract Medical International GmbH, Dresden (DE)

(*) Notice: Subject to any disclaimer, the term of this patent is extended or adjusted under 35 U.S.C. 154(b) by 687 days.

(21) Appl. No.: 12/514,092

(22) PCT Filed: Nov. 9, 2007

(86) PCT No.: PCT/US2007/084220
§ 371 (c)(1),
(2), (4) Date: Jan. 14, 2010

(87) PCT Pub. No.: WO2008/076548
PCT Pub. Date: Jun. 26, 2008

(65) Prior Publication Data
US 2010/0114306 A1 May 6, 2010

Related U.S. Application Data

(60) Provisional application No. 60/865,023, filed on Nov. 9, 2006, provisional application No. 60/939,905, filed on May 24, 2007.

(51) Int. Cl.
*A61F 2/24* (2006.01)

(52) U.S. Cl.
USPC ............................................. 623/2.11

(58) Field of Classification Search
USPC ................ 623/2.11; 606/139, 144, 148, 151, 606/191; 607/130
See application file for complete search history.

(56) References Cited

U.S. PATENT DOCUMENTS

| | | | |
|---|---|---|---|
| 5,616,149 | A | 4/1997 | Barath |
| 6,726,651 | B1 | 4/2004 | Robinson et al. |
| 7,077,801 | B2 | 7/2006 | Haverich |
| 7,373,207 | B2 * | 5/2008 | Lattouf ................. 607/130 |
| 7,490,580 | B2 | 2/2009 | Hanai et al. |
| 2005/0148815 | A1 | 7/2005 | Mortier et al. |
| 2005/0177181 | A1 | 8/2005 | Kagan et al. |
| 2006/0241544 | A1 | 10/2006 | Haverich |

FOREIGN PATENT DOCUMENTS

WO WO-2004/007355 A1 1/2004

* cited by examiner

*Primary Examiner* — Gregory Anderson
(74) *Attorney, Agent, or Firm* — Novak Druce Connolly Bove + Quigg LLP

(57) ABSTRACT

A method for performing cardiovascular and surgical procedures includes providing a conduit in the form of a graft/canula placed using balloon dilatation catheter and providing a fixing mechanism for the graft/canula. At least one opening is formed through a wall of the heart substantially at the apex. The escape of blood is prevented through the use of the fixing mechanism. Each of these steps is performed while the heart is beating.

29 Claims, 13 Drawing Sheets

Insertion system prior to balloon dilitation of myocardium repeat 3 more times for total of 4 anchors insertion system prior to balloon dilitation of myocardium insertion system after to balloon dilitation of myocardium canula in place graft/canula placed - balloon cath. and rear valve assembly removed

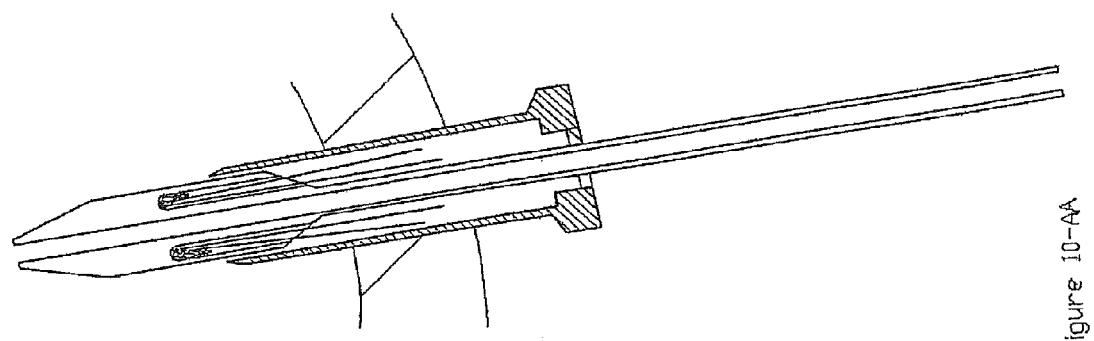
figure 10-AA
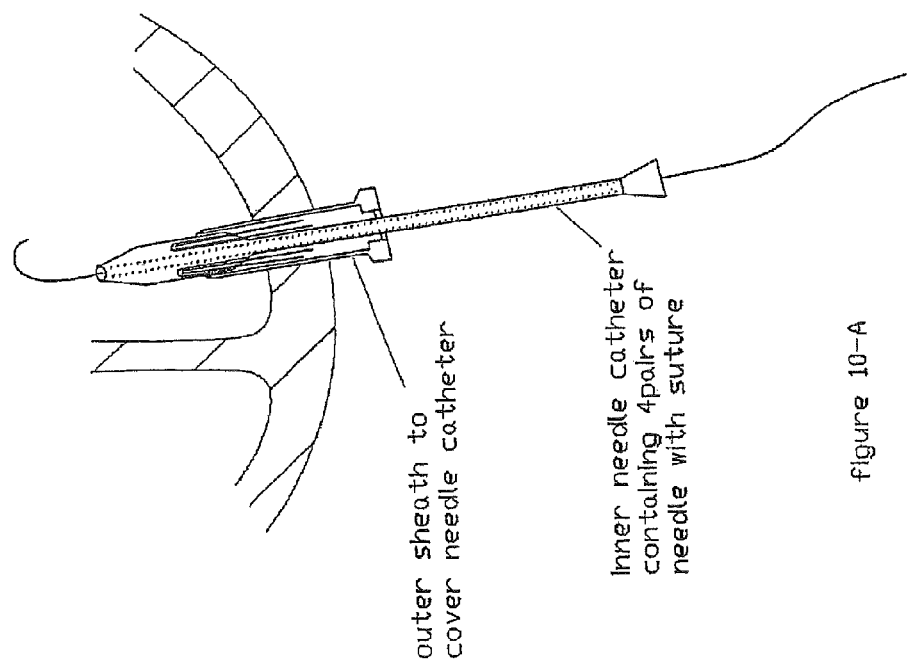
outer sheath to cover needle catheter
Inner needle catheter containing 4pairs of needle with suture
figure 10-A

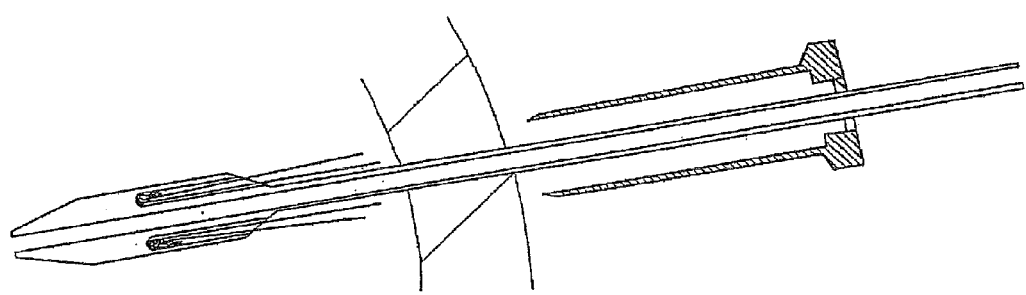
figure 10-BB
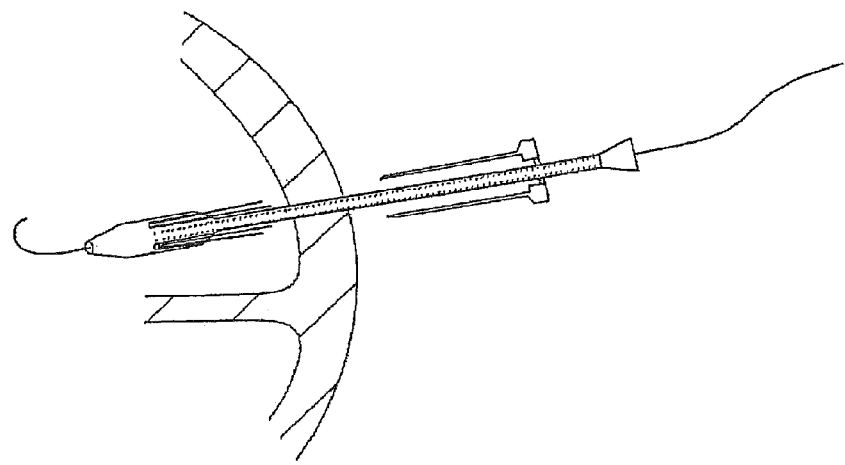
figure 10-B

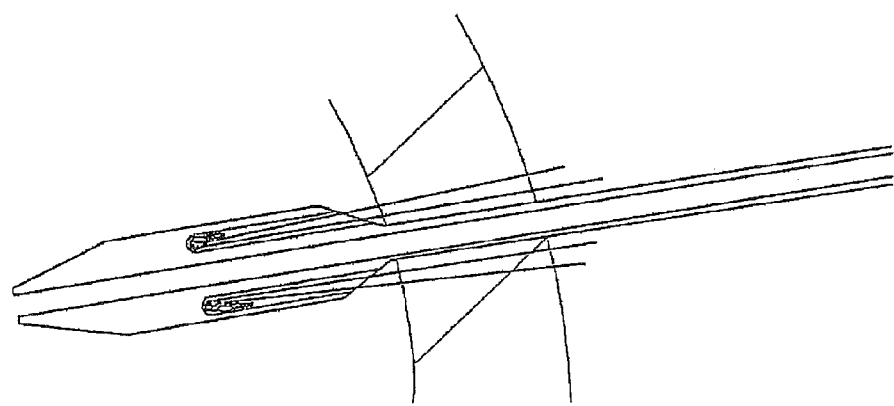
figure 10-CC
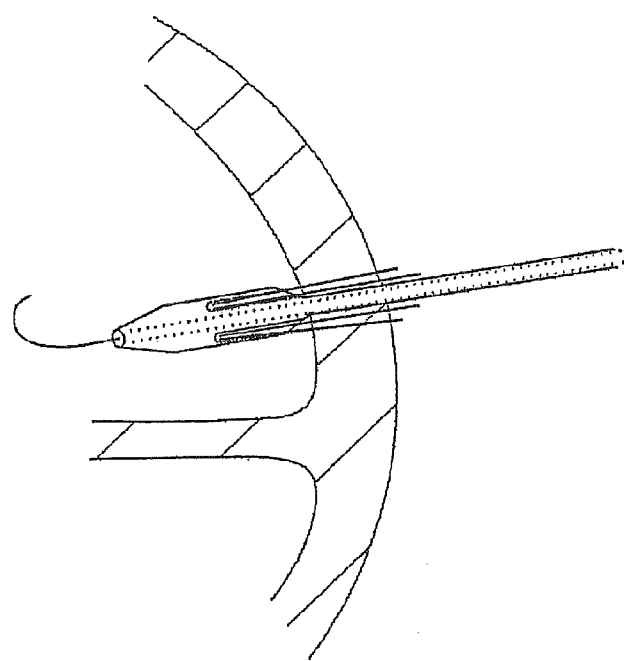
figure 10-C

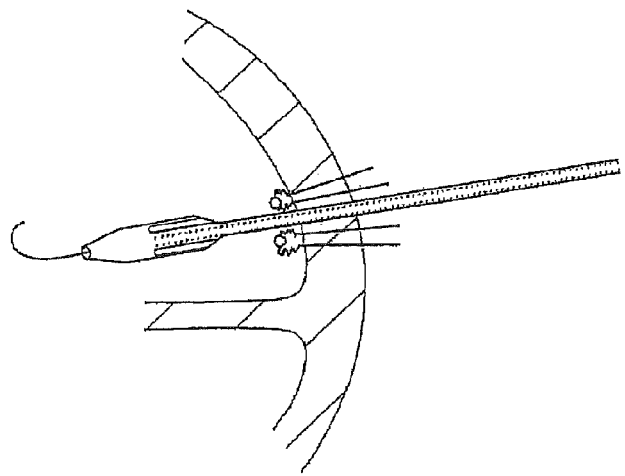
figure 10-D
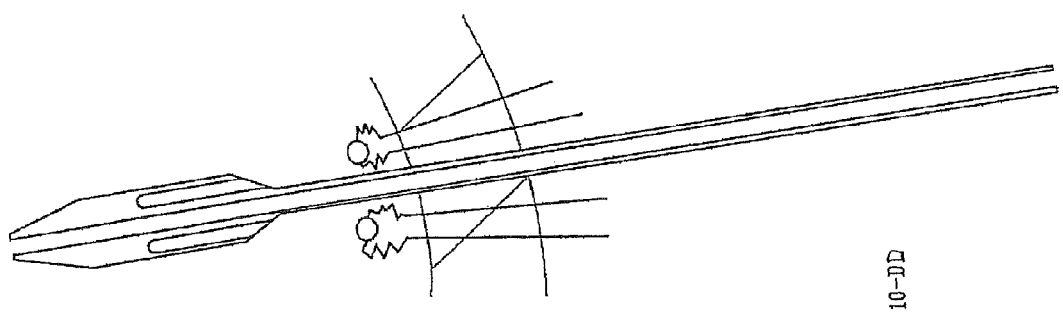
figure 10-DD

CARDIOVASCULAR PROCEDURES

BACKGROUND OF INVENTION

This invention relates generally to devices and methods for performing cardiovascular and surgical procedures. Various cardiovascular, surgical and other interventional procedures, including repair or replacement of aortic, mitral and other heart valves, repair of septal defects, pulmonary thrombectomy, coronary artery, bypass grafting, and neurovascular procedures, may require general anaesthesia, heart-lung machine ("on pump"), cardiopulmonary bypass, or arrest of cardiac function and treatment on the open chest.

In particular, this invention is concerned with the area aortic valve replacement procedure and focus is in patients with severely stenosed or damaged aortic valves. In the first instances, this new procedure will be performed on very sick patients who are not candidates for normal aortic valve replacement under normal open chest surgery where the patient is put on a heart-lung bypass machine. In the future, this invention could become the preferred method for placing an aortic valve in all patients since it is less invasive and better for the patient since it can be done on the beating heart through a thorocotomy instead of a sternotomy.

The invention also has applicability for 1) placement of apical grafts/canulas for Ventricular Assist Devices (VAD's), 2) for bypassing the mitral valve by creating a graft/canula with valve between the left atrium and left ventricle and 3) for creating access to the heart or to create a "port" through which other devices can be transferred or passed through. Such devices can be without any limitation heart valves, devices for repairing heart valves, other heart catheters, fluids.

Known techniques for performing major surgeries such as coronary artery bypass grafting and heart valve repair and replacement have generally required open access to the thoracic cavity through a large open wound, known as a sternotomy. Typically, the sternum is cut longitudinally (a median sternotomy), providing access between opposing halves of the anterior portion of the rib cage to the heart and other thoracic vessels and organs. An alternate method of entering the chest is via a lateral thoracotomy, in which an incision, typically 10 cm to 20 cm in length, is made between two ribs.

In particular this invention relates to the aortic valve replacement procedure, wherein the method of entering the chest is via a lateral thoracotomy and while the heart is beating, which is less invasive than through the sternum.

As noted, the invention also has applicability to VAD's, to bypassing the mitral valve and to accessing the heart. Such bypassing techniques could not only be used for aortic valve replacement but also for any native valve replacement via a "bypass" circuit.

Risks and complications associated with open-heart surgery, which involves the use of cardiopulmonary bypass, aortic cross-clamping and cardioplegic arrest, are well known.

Within recent years, minimally invasive types of procedures for coronary artery bypass surgery have been developed which do not require stopping the patient's heart and the use of cardiopulmonary bypass. While attempts have been made to treat aortic valves off-pump via endovascular procedures, e.g., endovascular balloon valvuloplasty, such procedures may provide only partial and temporary relief for a patient with a stenotic valve. Moreover, the rapid restenosis and high mortality following balloon aortic valvuloplasty have led to virtual abandonment of this procedure.

It should be noted that "percutaneous" methods for putting in new aortic valves are under development. However, there still exists problems during these "catheter-based"/"Percutaneous" procedures. In these procedures, the catheter must go through the aortic arch and in many cases this area and the aortic valve itself is very stenosed and calcified. So there is a very big risk of dislodging these calcified parts thus causing a stroke. Stroke from regular aortic valve replacement is a well known complication and occurs in 6-7% of procedures. By using a by-pass, any contact is avoided with the calcified aortic arch and the native vessel thus eliminating the risk of stroke in these patients.

Thus, there is an ongoing need for minimally invasive devices and techniques for treating patients suffering from diastolic dysfunction and directed to aortic valve replacement procedure. There is also a need for improved VAD placement, for bypassing the mitral valve and for accessing the heart. As such, it is desirable to provide such a procedure which is relatively simple and is easier to perform than conventional cardiovascular or surgical procedures and reduces the time and cost of the procedure. Moreover, it is desirable to provide such devices and procedures that obviate the need for cardiopulmonary bypass, can be used on a beating heart, involves endovascular or less invasive surgical techniques, and can be used by surgeons.

SUMMARY OF THE INVENTION

The present invention is directed to an approach for preparing a patient's heart for cardiac procedures which does not require a grossly invasive thoracotomy.

Some of the important advantages of the invention are:
No need for extracorporeal support;
No coring of the heart wall and thus no tissue loss;
Minimal blood loss;
No direct manipulation of diseased/calcified structures with the effect of possibly reducing thromboembolic events; and
Reduced procedure times.

An object of the present invention is to provide a new method for performing a cardiovascular operation.

These and other objects of the present invention will be apparent from the drawings and detailed descriptions herein.

THE DRAWINGS

FIGS. 1-9 are cross-sectional views schematically illustrating the various steps in one practice of this invention;

FIGS. 10-A through 10-E illustrate an alternative procedure to that shown in FIGS. 1-9; and FIGS. 11-13 schematically illustrate the various steps of accessing the LV apex in accordance with this invention.

DETAILED DESCRIPTION

This application is based on provisional application Ser. No. 60/865,023 filed Nov. 9, 2006 and Ser. No. 60/939,905 filed May 24, 2007, all of the details of which are incorporated herein by reference thereto.

In general the present invention includes various aspects relating to procedures such as the insertion for the ventricular apex graft/canula. In one aspect of this invention a catheter is provided.

The catheter comprises an elongate body having a proximal end and a distal end. In a preferred embodiment the catheter is a balloon dilatation catheter.

The graft/canula can be metal tube which is already expanded, self-expandable or expanded by means of a balloon or similar device (like a stent), and can be provided with various fixing mechanisms to anchor it in position, such as expandable legs, hooks, barbs, flanges, collars, loops, wires, flares, suture holes and the like. The graft/canula is normally covered in Dacron or other known graft type fabric material. The fixing mechanisms can be adapted to anchor the conduit in the heart wall. The conduit can be formed from a plurality of rings, which can be connected to provide stability. The conduit can include a valve in its interior.

Moreover, the fixing means are adapted in such a way in order to prevent the escape of blood. Hence, the fixing means refer also to a sealant.

Therefore in one aspect the present invention relates to a method comprising the steps:

providing a conduit by means of a balloon dilatation catheter, comprising fixing means, forming at least one opening through a wall of the heart substantially at the apex, preventing the escape of blood by means of said fixing means, performing each of the steps, while the heart is beating.

The preferred embodiments described herein below depict methods for delivering a conduit into the myocardium to create a passageway between the left ventricular apex and the descending aorta. In addition, the delivery methods described herein pertain to the placement of conduits and other devices partially through the myocardium, as well as for valve replacement and similar applications. The procedure can be used to create access to the heart or to create a "port" through which other devices can be placed.

The principles of the present invention are not limited to left ventricular conduits, and include conduits for communicating bodily fluids from any space with the preferred fluid communication conduits, and other non-myocardial and even non-cardiac fluid communication are preferred as well, such as blood vessels, which are part of the cardiovascular system and function to transport blood throughout the body, in particular arteries and veins, carry blood away from or towards the heart, respectively. With respect to the walls of the heart (and more specifically the term "heart wall"), the preferred conduits and related methods are capable of fluid communication through all such walls including, without limitation, the pericardium, epicardium, myocardium, endocardium, septum, or any blood vessel etc. As noted the invention creates the ability to create the access or port to the heart for other procedures.

The preferred conduits and related methods disclosed herein can also provide complete passages or partial passages through bodily tissues. In this regard, the conduits can comprise stents, shunts, or the like, and therefore provide a passageway or opening for bodily fluid such as blood. Thus, although many of the preferred embodiments may describe stents or shunts, it will be appreciated that other types of conduits may be used as well. Moreover, the conduits are not necessarily stented or lined with a device but can comprise mere tunnels or openings formed in the tissues of the patient.

To achieve some or all of the objects of the present invention, in particular creating a myocardial passageway between the left ventricle LV and the descending aorta for disposition of a conduit therein or forming an opening, requires a delivery system capable of directing the necessary devices to and into the myocardium. As described in further detail below, the suitable delivery system: (1) provides access to the insertion site adjacent the myocardium; (2) creates an angled bend for transverse insertion of devices into the myocardium; and (3) directs devices into the myocardium for creation of the myocardial passageway.

In a preferred embodiment of the invention, the apical opening or formed passageway in accordance with present invention is placed in the apex of the heart.

The following is an insertion procedure for the ventricular apex graft/canula for creating a valved circuit between the left ventricular apex and the descending aorta in patients requiring a new aortic valve for example in the case of severe aortic valve stenosis. Reference will be made to the accompanying drawings.

FIG. 1: Insert a standard 18 Ga needle into the apex of the left ventricle; confirm placement under x-ray/fluoroscopy and pulsatile leaking of blood from the needle. Then place a Guide wire (0.025" to 0.035" for example) with soft "J" end to avoid damage to the structures in the heart.

FIG. 2: Remove the needle leaving in the Guide wire and then place a standard (8-10 for example) Fr sheath valved introducer with dilator over the Guide wire as shown.

Next, remove the dilator from the sheath/dilator assembly while leaving the Guide wire in place as shown in FIG. 3.

FIG. 3A: Advance the curved "needle guiding catheter" through the sheath introducer until the curve is out of the end of the sheath. This can be confirmed by having a distance mark on the needle guide catheter or visually under x-ray/fluoroscopy.

Next, pull tight the pull wire which is in the needle guiding catheter and exits the needle guiding catheter right at the proximal part of the curve and is fixed to the very tip of the needle guiding catheter. Tightening this pull wire will help keep the needle guiding catheter in its shape and keep it rigid while advancing the needles with the inner anchors which will be described next. (Steerable guide catheters with internal pull wires can also be used.)

FIG. 4 shows the advancement through the myocardium (from inside the ventricle to outside) of 2 needles that are feed through the entire length of the needle guide catheter (or pre-placed in the needle guide catheter).

Fixed to the back end of the 2 needles which are now placed through the myocardium is a long suture with a Teflon (or other material) anchor/plug at the mid-point of the suture. This suture with anchor will be pulled through the needle guide catheter and sheath and be pulled up against the inside of the heart wall around the apex of the ventricle. The key here is that 2 needles are used which creates 2 exit points for the 2 sutures and better secures the anchor from being pulled out through the heart wall. This is what creates the "inner anchor" for the graft canula. 4-6 of these anchors can be placed for securing the inner anchors system to the outer flange of the graft/canula.

FIG. 5 shows an example of an inner anchor in place on the inside of the left ventricle with suture through the heart wall. Prior to cutting the needles off of the sutures with anchors, the needle should be placed through the outer flange.

Next, with 4-6 inner anchors in place, the physician can now hold and secure the total left ventricular apex area of the heart by pulling on the sutures which are through the heart wall, exiting from the myocardium and attached to the inner anchors. The 4-6 anchors should be placed in a circle around the apex for example at 12, 3, 6 and 9 on the clock when looking directly at the apex. Using 6 would just spread the anchors more around the "clock".

FIG. 6: While holding the 4-6 suture/inner anchors, the physician then advances or inserts the 2 balloon-catheter system shown over the Guide wire. Before inserting the rear fixation balloon should be inflated inside the graft canula as shown so that the entire assembly becomes fixed together. Without doing this, the insertion catheter would slide independent of the graft canula and this would make advancement of the catheter with dilatation balloon as shown. By having these inner anchors in place and being able to hold tight and fix the apex and the insertion catheter with balloons slides into myocardium easily. Without holding the anchor/suture and fixing the apex, the apex tends to "push away" from you as you try to push it in and insertion is very risky and requires a lot of manipulation.

FIG. 6: The overall insertion system with graft/canula is made up of a number of parts which will be described here:

2 Balloon Catheter

This is the main part of the whole system. The end balloon is used for dilating the myocardium so that the graft canula can be inserted into place as shown in FIG. 8. The rear balloon is a fixation balloon and is used for grabbing or holding the graft/canula so that it can be pushed into the hole created by the dilatation balloon.

This will be a 3 lumen catheter with lumens for:
2—inflating independently each balloon and
1—for inserting the system over a guide wire.

As illustrated in FIG. 6, over the dilatation balloon and extending over the end "lip" or edge of the graft/canula is a "skirt". This skirt covers the gap between the inflated dilatation balloon and the end edge of the graft/canula. Without this skirt, the assembly might tend to get "caught up" as you try to advance it into the hole created by the dilatation balloon. The invention, however, could also be practiced without a skirt.

Graft/Canula

The graft/canula is made up of a Dacron (or similar) material. The end which will sit in the wall of the heart is made up of a stainless steel (or other material) tube or canula. This tube will be metal so as to resist the myocardium from crushing the graft/canula when the dilatation balloon is deflated. A very strong stent could also be used in place of this metal tube.

The outer flange is a ring around the end of the metal tube and it is made out of Dacron material.

Just after the metal tube and flange is a spring which is sewn to the graft. This spring is there to prevent kinking of the graft once it is in place in the body. The spring is schematically illustrated by the two sets of circles between the flange and the rear valve assembly in FIG. 6.

Then after the spring is just Dacron tube material and then this will be used to sew the valve in place and to attach to the descending aorta.

Rear Valve Assembly

This is a very large valve through which the 2 balloon catheter is placed. This is fixed to the non-spring portion of the Dacron tube and this is used to prevent excessive bleeding after the dilatation balloon and fixation balloons are deflated and removed.

Now the 2 balloon/insertion catheter is advanced over the guide wire into the hole which was created by the sheath introducer. The 2 balloon catheters can also be placed through a "peel-able" sheath. At this stage the rear fixation balloon is inflated and locked to hold the system all together and the end dilatation balloon is deflated and a vacuum is pulled to try and make it as flush with the catheter as possible.

The dilatation balloon is then put in place in the heart wall as shown in FIG. 6.

Figure 1:
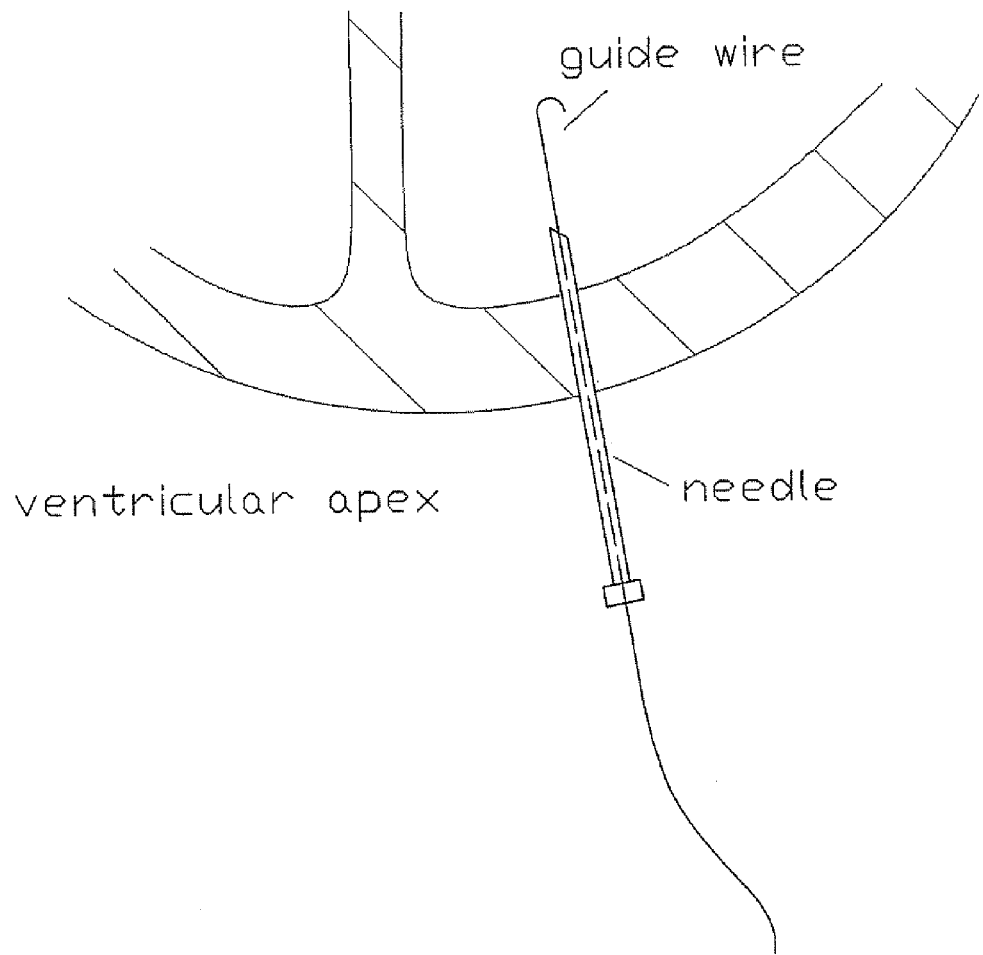
Figure 2:
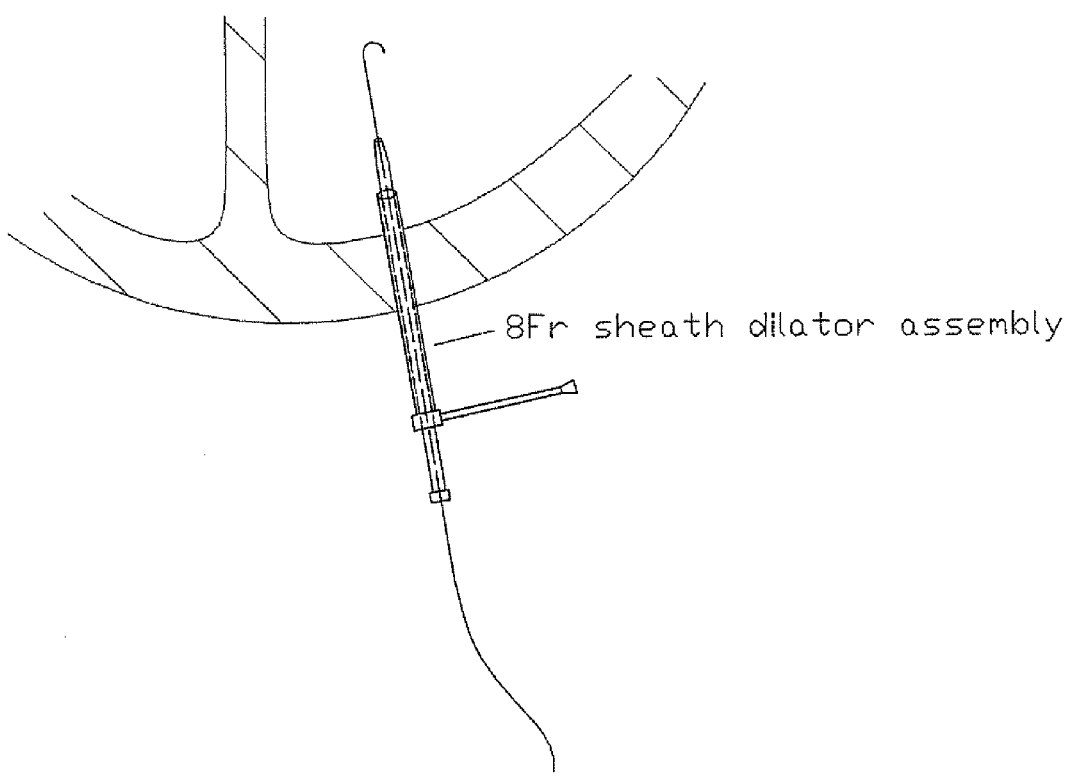
Figure 3:
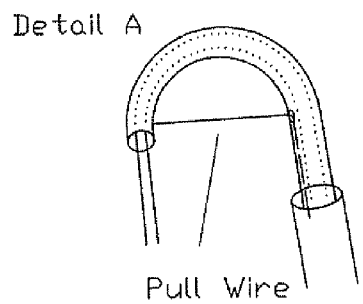
Figure 3:
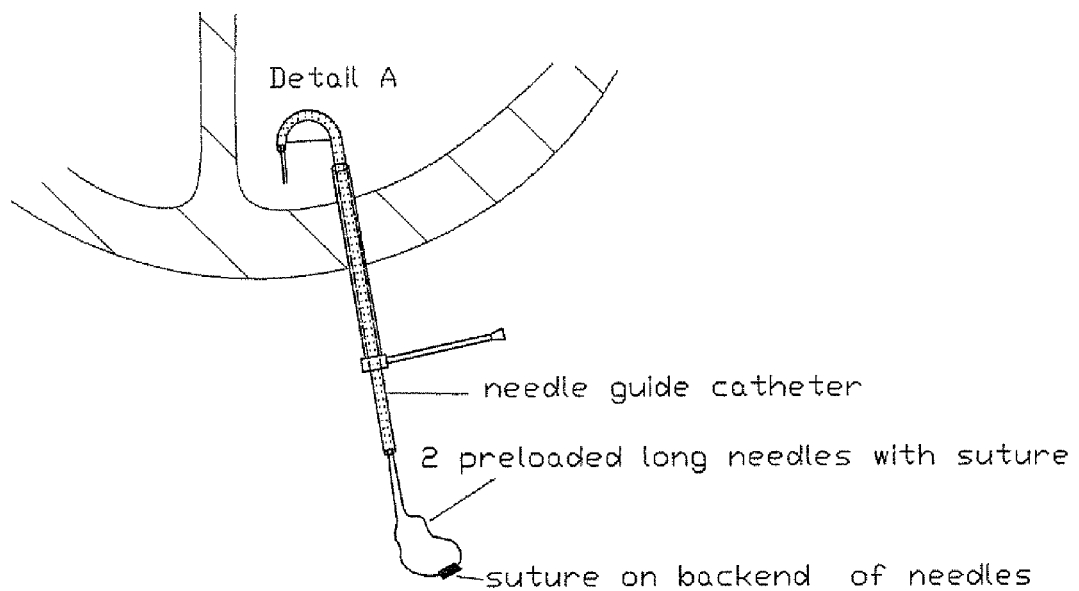
Figure 4:
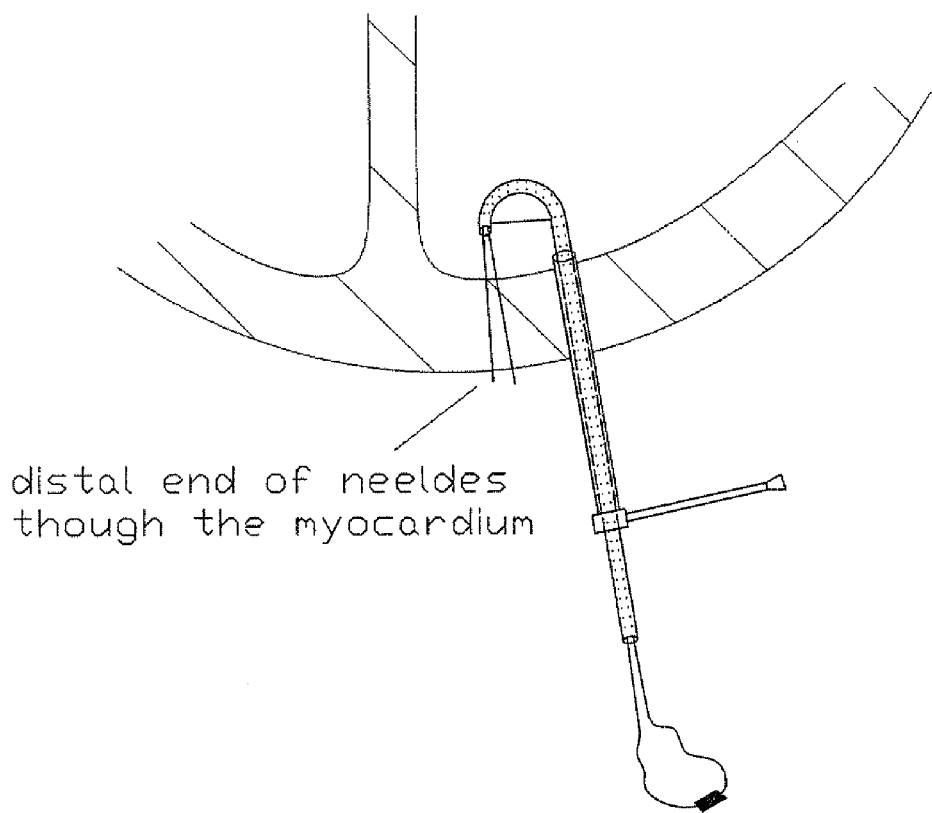
Figure 5:
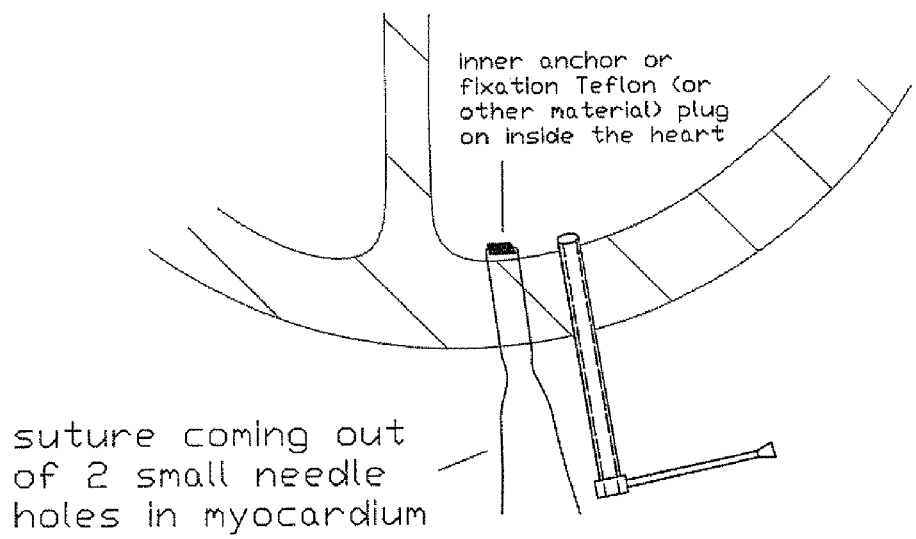
Figure 6:
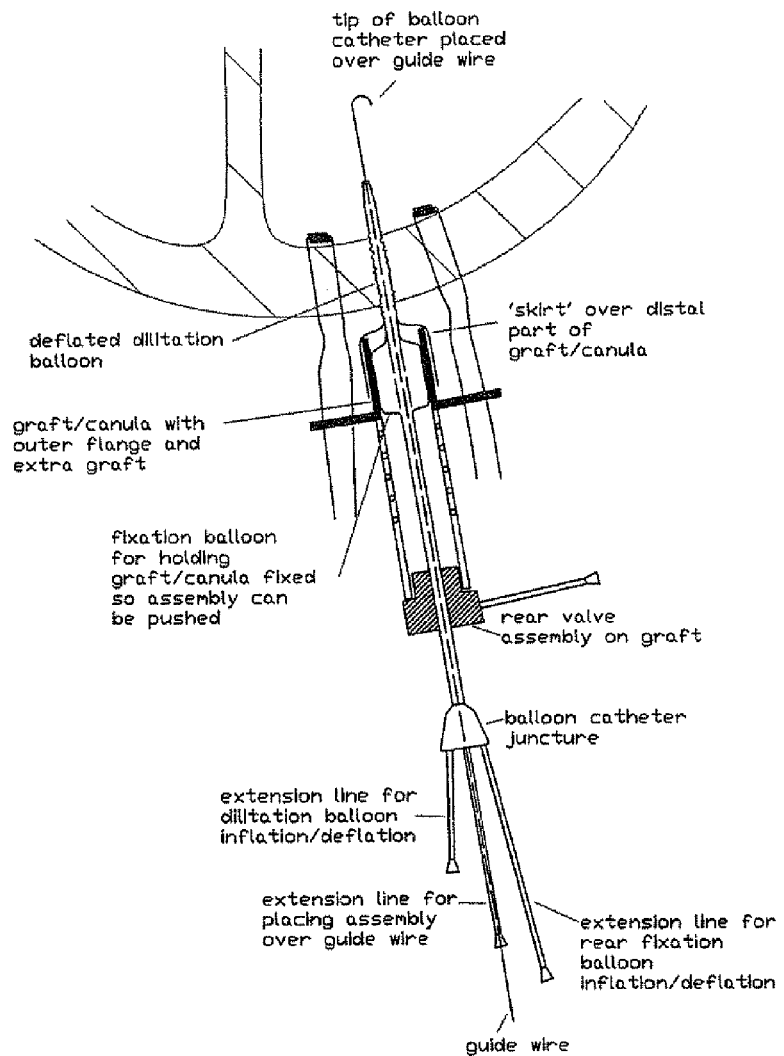
Figure 7:
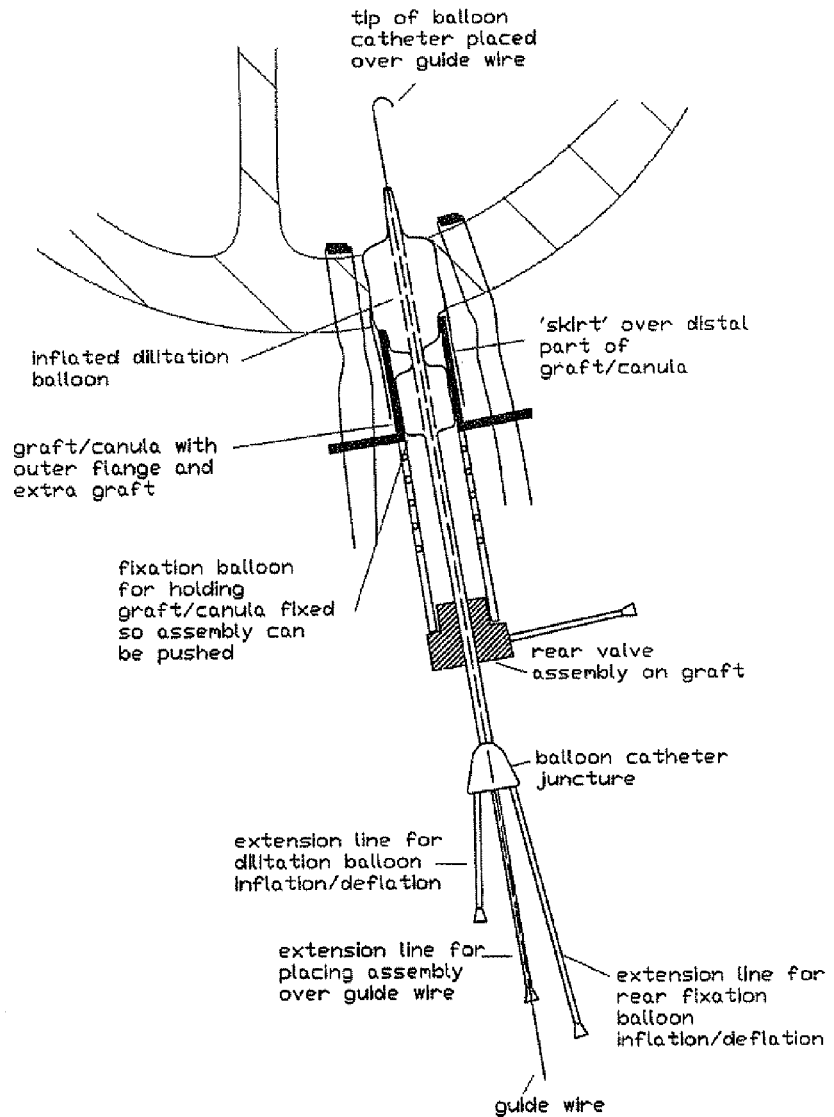
FIG. 7 shows the same position as FIG. 6 but with the dilatation balloon dilating the myocardium creating the hole into which the graft/canula will be pushed.
Figure 8:
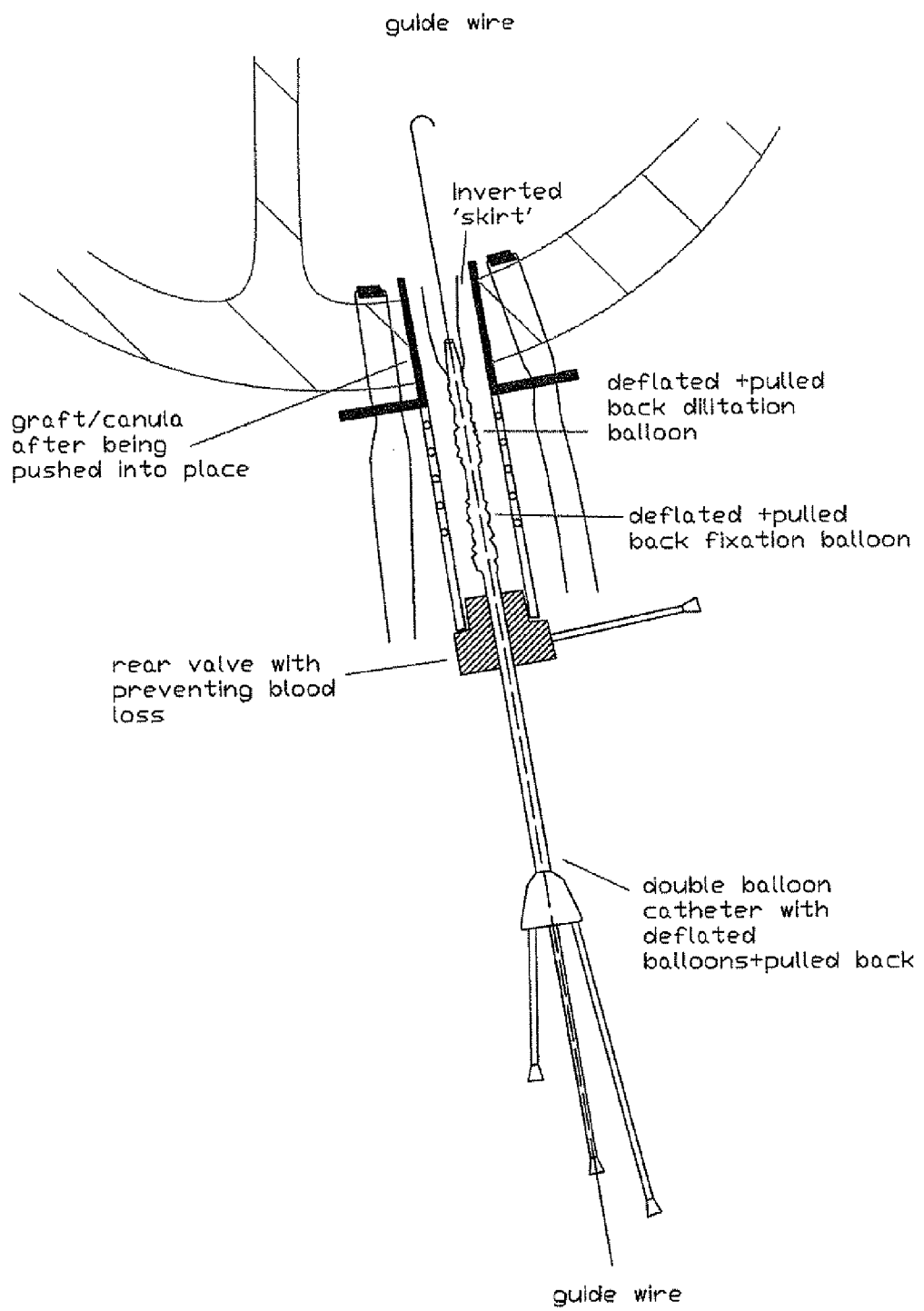
FIG. 8 shows the graft canula pushed into place in the heart wall and the 2 balloons on the catheter deflated and the entire catheter partially pulled back towards the rear valve. Note that the skirt which was over the dilatation balloon and covering the end edge (lip) of the graft canula must invert in order to get it pulled back and off the end edge of the graft/canula.

It is important to note that the long needles with suture and plug must be placed though the outer flange of the graft/canula. The needles are then cut off the suture leaving the inner anchor with suture through the myocardium and through the outer flange as shown in FIG. 8.

Next, the 2 balloon catheter is pulled back until the rear balloon inside the rear valve. The rear valve is then cut off the Dacron graft and the graft is clamped.

Figure 9:
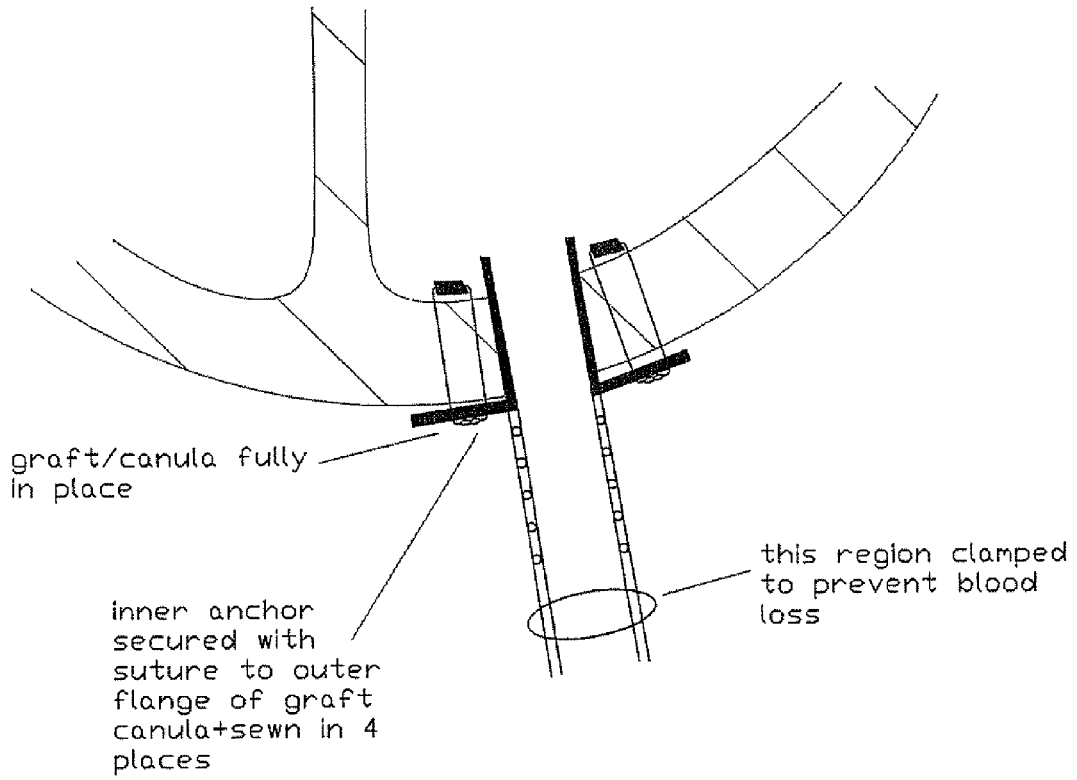

FIG. 9 shows the graft canula in place without the balloon catheter and with the anchors with suture sewn tight to the outer flange to "sandwich" the myocardium to prevent bleeding and fully secure the graft/canula. This is the key for reducing bleeding which is a huge complication for a procedure like this. It is thus possible to place the suture and Teflon plug on the inside of the heart and sew it to the outer ring in a sandwiched fashion. It is also possible to simply sew the outer ring to the outside of the heart.

FIGS. 10-A through 10-E illustrate a variation of the procedure shown in FIGS. 1-9. In that regard, FIGS. 1-9 might be considered as using a needle guide catheter to place the needles with suture from the inside of the heart to the outside of the heart. In such procedure the needle guide catheter is put in and then steered or bent back to face the heart. The alternative procedure shown in FIG. 10 uses one catheter which has needles that already point backwards similar to an umbrella and when the surgeon pulls the catheter back the needles stick through the heart wall. This would be much quicker and easier to accomplish than the procedure of FIGS. 1-9.

As shown in FIG. 10-A the inner needle catheter containing, for example, four pairs of needles with suture is disposed within the outer catheter sheath which covers the needle catheter. The outer sheath is removed as illustrated in FIG. 10-B when the needles are completely in the heart beyond the heart wall. The catheter is then pulled toward the wall so that the needles penetrate the wall and become anchored to the wall as shown in FIGS. 10-C and 10-D. Thus, when the catheter is pulled back there is a firm attachment. As illustrated in FIG. 10-E the sutures at the end of the needles are joined by an inner anchor similar to FIG. 5.

In accordance with a further aspect of this invention techniques are provided for placement of apical grafts/canulas for Ventricular Assist Devices (VAD's). Such techniques could be used, for example, for implantation of a left Ventricular Assist Device (LVAD). For LVAD implants a conduit is placed from the left ventricular apex to the aorta or to another major artery. Reference is made to U.S. Pat. No. 7,077,801, all of the details of which are incorporated herein by reference thereto. As regards that patent the curved arrow 46 in FIG. 2A of that patent shows where an LVAD could be placed in accordance with this invention. With the balloon dilatation method it is possible to put in an LVAD on a beating heart which would be considered revolutionary.

A further aspect of this invention is for bypassing the mitral valve or any native heart valve. The mitral valve gets stenosed and it would be desirable to bypass this in the manner done to bypass the aortic valve. This would be done by shunting the blood from the left atrium (upstream) to the LV Apex (downstream). So, basically the blood would then flow into the LV Apex instead of out of it. Such technique could be practiced in order to put a conduit with a valve where it would be desired to bypass a native valve and provide a new valve in the conduit. Bypassing the mitral valve would be done by creating a graft/canula with a valve between the left atrium and the left ventricle. In general, the techniques of this invention provide placing a graft in the heart, mainly for bypassing a native valve (and thus in effect implanting an artificial one). The method, however, can be broadly practiced by placing the graft in any chamber of the heart, such as, for example, the right and left atria and ventricles.

Thus, one aspect of the invention is accessing the ventricular apex. This would be done by making an access in the ventricular apex which allows for access to the heart with minimal blood loss. Thus, in addition to the ability to put in a graft or conduit an aspect of the invention also involves the ability to obtain access to the apex. This could be useful in situations where the physician/surgeon wants to access the heart through the apex of the ventricle and have a blood-less, stable access while another procedure is being done. The invention thus provides for gaining access to the heart with minimal blood loss, stability, easy closing and no coring of the heart. (i.e., no removal of heart tissue)

FIGS. 11-13 schematically illustrate a practice of the invention for accessing the LV Apex to use it as a stable access point for delivering other items into the heart.

FIG. 11 illustrates the step in the procedure involving graft placement. As shown therein the graft/canula is fully in place. A large bore valve is clamped to the graft to prevent blood loss. FIG. 12 shows the graft with the sheath system and illustrates the graft/canula fully in place. FIG. 13 illustrates the graft with the sheath system and canula where the canula hub provided with a balloon and guide wire is included in the system. This procedure could be practiced using known components. FIGS. 11-13 illustrate use of the graft/canula shown, for example, in FIGS. 6-9.

An advantageous feature of the invention is in its fixing/anchor system and providing the canula through the apex of the heart and also in the general use of such a canula in the treatment of cardiovascular/heart diseases. Reference is made to PCT application WO200407355A1, all of the details of which are incorporated herein by reference thereto. Such application is pertinent with regard to the use of the apex as the starting point for a cardiovascular/heart diseases. With the present invention an advantageous feature is the use of an approach with the balloon as the "dilatation" part. This can be done in a somewhat bloodless manner to open up the apex without removing any tissue. Normally to place a canula or conduit one would have to "core" out part of the heart which is very undesirable since it can cause significant bleeding while also removing healthy tissue from a very sick heart. In contrast, the present invention provides the advantages of eliminating the need for extracorporeal support, eliminates coring of the heart thus having no tissue loss, minimizes blood loss, provides for no direct manipulation of disease/calcified structures with the effect of possibly reducing thromboembolic events and provides reduced procedure times.

As is apparent from the foregoing description among the advantages of the invention are the uses of new catheters which more easily get the needles and thus the sutures with inner anchors in the heart. A particular advantageous practice of the invention is putting the graft/canula in the ventricle. But the graft/canula also should be connected to the aorta to complete the circuit.

Thus, one aspect of the invention is the use of a balloon dilatation catheter for forming at least one opening through a wall of the heart substantially at the apex in providing a conduit in the form of a graft/canula placed, wherein the said catheter comprises a fixing mechanism preventing the escape of blood through use of the fixing mechanism and performing the use of said catheter while the heart is beating.

Such a use of the balloon dilatation can be carried out in all further embodiments, methods and assemblies hereby disclosed.

The embodiments illustrated and described above are provided merely as examples of certain preferred embodiments of the present invention. Other changes and modifications can be made from the embodiments presented herein by those skilled in the art without departure from the spirit and scope of the invention, as defined by the appended claims. Accordingly, it is to be understood that the drawings and descriptions herein are proffered by way of example to facilitate comprehension of the invention and should not be construed to limit the scope thereof.

What is claimed is:

1. A cardiovascular/surgical method comprising the following steps:
   providing a conduit in the form of a craft/canula placed using a balloon dilatation catheter,
   providing the catheter with a fixing mechanism,
   forming at least one opening through a wall of the heart substantially at the apex,
   preventing the escape of blood through use of the fixing mechanism, and
   performing each of the steps while the heart is beating, wherein the hole through the wall of the heart is created by a needle with a guide wire located in the needle and extending into the heart, removing the needle with the guide wire remaining in place, placing a sheath valve introducer with dilator over the guide wire, removing the dilator while leaving the guide wire in place, advancing a curved needle guiding catheter through the sheath valve introducer until the curve is out of the sheath, pulling tight a pull wire fixed to the tip of the needle guiding catheter, tightening the pull wire to maintain the shape of the needle guiding catheter and be rigid, and advancing needles with inner anchors toward the myocardium to create needle holes in the myocardium, passing sutures through the needle holes, fixing the anchors to the sutures inside the heart to create a fixation plug inside the heart and prevent the sutures from passing completely through the myocardium, advancing an insertion/balloon-catheter system containing an end balloon and a fixation balloon through the graft/canula, dilating the myocardium with the end balloon, disposing a rear valve assembly in the graft/canula to prevent blood loss, and anchoring the free end of the sutures which extend through and are located externally of the myocardium.

2. The method of claim 1 wherein the forming of the apical opening is performed without the need to remove any heart tissue.

3. The method of claim 1 wherein the graft/canula which is placed in the apical opening after balloon dilatation has inner flanges to which sutures are attached from the outside of the heart to secure the sutures to a moveable outer flange on the outer part of the canula/graft and thus sandwiching the heart wall between the inner and outer flanges making a very secure, leak tight connection.

4. The method of claim 3 where anchors are pushed through needles which are placed through the heart wall and used to secure the sutures.

5. The method of claim 1 where anchors are secured on the inside of the heart wall.

6. The method of claim 1 wherein the method is used for a surgical procedure selected from the group consisting of repair or replacement of aortic, mitral and other heart valves, replacement of septal defects, pulmonary thrombectomy, coronary artery, bypass grafting and neurovascular procedures, cardiopulmonary bypass, arrest of cardiac function and treatment on the open chest.

7. The method of claim 1 wherein the method is used for the placement of the apical grafts/canulas for ventricular assist devices.

8. The method of claim 1 wherein the method is used for bypassing the mitral valve by creating the graft/canula with a valve between the left atrium and the left ventricle.

9. The method of claim 1 wherein the method is used for bypassing a native heart valve by placing the graft/canula in a chamber of the heart.

10. The method of claim 9 wherein blood is shunted from the left atrium to the LV apex so that blood flows into the LV apex.

11. The method of claim 1 wherein the method is used for accessing the ventricular apex.

12. The method of claim 1 wherein the method is performed without extracorporeal support and without the coring of the heart and without direct manipulation of disease/calcified structures, and the method is performed with minimal blood loss.

13. The method of claim 1 wherein the heart wall is selected from the group consisting of pericardium, epicardium, myocardium, endocardium and septum or any blood vessel wall.

14. The method of claim 13 wherein the method is used for delivering a conduit into the myocardium to create a passageway between the left ventricular apex and the descending aorta.

15. The method of claim 1 wherein the opening through the wall creates a port through which other devices can be placed.

16. The method of claim 1 wherein the graft/canula includes an annular flange externally of the graft/canula and the free ends of the sutures are secured to the outer flange to create a sandwich comprising the myocardium disposed between the outer flange and the inner anchor of the sutures.

17. A cardiovascular/surgical method comprising the following steps:
providing a conduit in the form of a graft/canula placed using a balloon dilatation catheter,
providing the catheter with a fixing mechanism,
forming at least one opening through a wall of the heart substantially at the apex,
preventing the escape of blood through use of the fixing mechanism, and
performing each of the steps while the heart is beating, wherein the opening through the wall is created by an inner needle catheter containing a plurality of needles with sutures, wherein the catheter is disposed in an outer sheath, removing the outer sheath to expose the plurality of needles, pulling the catheter backwards to move the needles into and through the wall of the heart and removing the needles with sutures from the catheter.

18. The method of claim 17 wherein the forming of the apical opening is performed without the need to remove any heart tissue.

19. The method of claim 17 where anchors are secured on the inside of the heart wall.

20. The method of claim 17 wherein the method is used for a surgical procedure selected from the group consisting of repair or replacement of aortic, mitral and other heart valves, replacement of septal defects, pulmonary thrombectomy, coronary artery, bypass grafting and neurovascular procedures, cardiopulmonary bypass, arrest of cardiac function and treatment on the open chest.

21. The method of claim 17 wherein the method is used for the placement of the apical grafts/canulas for ventricular assist devices.

22. The method of claim 17 wherein the method is used for bypassing the mitral valve by creating the graft/canula with a valve between the left atrium and the left ventricle.

23. The method of claim 17 wherein the method is used for bypassing a native heart valve by placing the graft/canula in a chamber of the heart.

24. The method of claim 23 wherein blood is shunted from the left atrium to the LV apex so that blood flows into the LV apex.

25. The method of claim 17 wherein the method is used for accessing the ventricular apex.

26. The method of claim 17 wherein the method is performed without extracorporeal support and without the coring of the heart and without direct manipulation of disease/calcified structures, and the method is performed with minimal blood loss.

27. The method of claim 17 wherein the heart wall is selected from the group consisting of pericardium, epicardium, myocardium, endocardium and septum or any blood vessel wall.

28. The method of claim 27 wherein the method is used for delivering a conduit into the myocardium to create a passageway between the left ventricular apex and the descending aorta.

29. The method of claim 17 wherein the opening through the wall creates a port through which other devices can be placed.

* * * * *